(12) United States Patent
Predick et al.

(10) Patent No.: US 10,117,750 B2
(45) Date of Patent: Nov. 6, 2018

(54) IMPLANT FOR BONE FIXATION

(71) Applicant: Life Spine, Inc., Huntley, IL (US)

(72) Inventors: Daniel P. Predick, Chicago, IL (US);
Garrett D. Lauf, Elgin, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/869,723

(22) Filed: Jan. 12, 2018

(65) Prior Publication Data

US 2018/0133019 A1 May 17, 2018

Related U.S. Application Data

(60) Division of application No. 14/819,761, filed on Aug. 6, 2015, now Pat. No. 9,889,014, which is a continuation-in-part of application No. 14/616,239, filed on Feb. 6, 2015, now Pat. No. 9,877,759.

(60) Provisional application No. 61/936,644, filed on Feb. 6, 2014.

(51) Int. Cl.
*A61B 17/80* (2006.01)
*A61F 2/42* (2006.01)

(52) U.S. Cl.
CPC ........ *A61F 2/4202* (2013.01); *A61B 17/8042* (2013.01); *A61B 17/8061* (2013.01); *A61B 17/8095* (2013.01); *A61F 2002/4212* (2013.01); *A61F 2002/4238* (2013.01)

(58) Field of Classification Search
None
See application file for complete search history.

(56) References Cited

U.S. PATENT DOCUMENTS

| | | | |
|---|---|---|---|
| 1,919,728 | A | 7/1933 | Kellogg |
| 2,383,141 | A | 8/1945 | Maage, Jr. |
| 2,401,856 | A | 6/1946 | Brock |
| 3,741,205 | A | 6/1973 | Markolf et al. |
| 4,175,555 | A | 11/1979 | Herbert |
| 4,298,993 | A | 11/1981 | Kovaleva et al. |
| 4,388,921 | A | 6/1983 | Sutter et al. |
| 4,794,918 | A | 1/1989 | Wolter |
| 4,808,185 | A | 2/1989 | Penenberg et al. |

(Continued)

FOREIGN PATENT DOCUMENTS

| | | |
|---|---|---|
| CH | 674927 A5 | 8/1990 |
| DE | 2933141 A1 | 4/1980 |

(Continued)

OTHER PUBLICATIONS

International Search Report for International Application No. PCT/US04/43172, dated Nov. 1, 2005, 4 pages.

(Continued)

*Primary Examiner* — Sameh Boles
(74) *Attorney, Agent, or Firm* — Foley & Lardner LLP

(57) ABSTRACT

A bone implant, particularly but not necessarily, for fixing bones of the foot is provided having body in the form of a crescent or arced shaped wedge, or a wedge in the shape of a crescent or arc. The crescent shaped wedge has bone screw bores that are each configured to hold a bone screw at a particular angle for receipt in a bone, eliminating the need to also use a plate. The crescent shape provides a graft area that allows introduction and retention of bone graft material to promote bone fusion. One or both tapered sides of the crescent shaped wedge may also have teeth, serrations or the like.

16 Claims, 12 Drawing Sheets

(56) References Cited

U.S. PATENT DOCUMENTS

| | | |
|---|---|---|
| 4,904,261 A | 2/1990 | Dove et al. |
| D313,471 S | 1/1991 | Bremer et al. |
| 5,197,839 A | 3/1993 | Willey et al. |
| 5,364,399 A | 11/1994 | Lowery et al. |
| 5,417,692 A | 5/1995 | Goble et al. |
| 5,514,180 A | 5/1996 | Heggeness et al. |
| 5,534,027 A | 7/1996 | Hodorek |
| 5,620,448 A | 4/1997 | Puddu |
| 5,766,251 A | 6/1998 | Koshino |
| 5,888,223 A | 3/1999 | Bray, Jr. |
| 5,951,558 A | 9/1999 | Fiz |
| 6,086,593 A | 7/2000 | Bonutti |
| 6,099,531 A | 8/2000 | Bonutti |
| 6,139,550 A | 10/2000 | Michelson |
| 6,152,927 A | 11/2000 | Farris et al. |
| 6,193,721 B1 | 2/2001 | Michelson |
| 6,224,602 B1 | 5/2001 | Hayes |
| 6,228,085 B1 | 5/2001 | Theken et al. |
| 6,234,034 B1 | 5/2001 | Ando |
| 6,235,034 B1 | 5/2001 | Bray |
| 6,258,089 B1 | 7/2001 | Campbell et al. |
| 6,273,889 B1 | 8/2001 | Richelsoph |
| 6,306,136 B1 | 10/2001 | Baccelli |
| 6,364,881 B1 | 4/2002 | Apgar et al. |
| 6,398,783 B1 | 6/2002 | Michelson |
| 6,402,756 B1 | 6/2002 | Ralph et al. |
| 6,413,259 B1 | 7/2002 | Lyons et al. |
| 6,423,063 B1 | 7/2002 | Bonutti |
| 6,428,542 B1 | 8/2002 | Michelson |
| 6,432,106 B1 | 8/2002 | Fraser |
| 6,436,146 B1 | 8/2002 | Hassler et al. |
| 6,447,544 B1 | 9/2002 | Michelson |
| 6,454,769 B2 | 9/2002 | Wagner et al. |
| 6,458,134 B1 | 10/2002 | Songer et al. |
| 6,503,250 B2 | 1/2003 | Paul |
| 6,533,786 B1 | 3/2003 | Needham et al. |
| 6,599,290 B2 | 7/2003 | Bailey et al. |
| 6,602,257 B1 | 8/2003 | Thramann |
| 6,620,163 B1 | 9/2003 | Michelson |
| 6,629,998 B1 | 10/2003 | Lin |
| 6,669,700 B1 | 12/2003 | Farris et al. |
| 6,695,846 B2 | 2/2004 | Richelsoph et al. |
| 6,730,127 B2 | 5/2004 | Michelson |
| D510,260 S | 10/2005 | Jennings et al. |
| 6,974,460 B2 | 12/2005 | Carbone et al. |
| 7,001,385 B2 | 2/2006 | Bonutti |
| 7,077,864 B2 | 7/2006 | Byrd et al. |
| 7,232,463 B2 | 6/2007 | Falahee |
| 7,780,670 B2 | 8/2010 | Bonutti |
| D625,977 S | 10/2010 | Watson et al. |
| 7,862,614 B2 | 1/2011 | Keller et al. |
| 7,862,616 B2 | 1/2011 | Lechmann et al. |
| 7,892,261 B2 | 2/2011 | Bonutti |
| 7,972,363 B2 | 7/2011 | Moskowitz et al. |
| 8,137,405 B2 | 3/2012 | Kostuik et al. |
| D658,046 S | 4/2012 | Austin |
| 8,182,539 B2 | 5/2012 | Tyber et al. |
| 8,419,778 B2 | 4/2013 | Barry |
| 8,419,797 B2 | 4/2013 | Biedermann et al. |
| 8,486,066 B2 | 7/2013 | Bonutti |
| 8,529,611 B2 | 9/2013 | Champagne et al. |
| 8,551,137 B2 | 10/2013 | Cohen et al. |
| 8,603,145 B2 | 12/2013 | Forton et al. |
| 8,690,944 B2 | 4/2014 | Bonutti |
| D706,127 S | 6/2014 | Hohmann, Jr. |
| 8,784,498 B2 | 7/2014 | Scheland |
| 8,795,363 B2 | 8/2014 | Bonutti |
| 8,852,280 B2 | 10/2014 | Armstrong et al. |
| 8,882,813 B2 | 11/2014 | Jones et al. |
| 8,956,417 B2 | 2/2015 | Bonutti |
| 9,017,412 B2 | 4/2015 | Wolters et al. |
| 9,044,341 B2 | 6/2015 | Bonutti |
| 9,072,562 B2 | 7/2015 | Weiner et al. |
| 9,358,122 B2 | 6/2016 | Soo |
| 9,364,342 B2 | 6/2016 | Walkenhorst et al. |
| 9,381,049 B2 | 7/2016 | McCormack et al. |
| 9,713,537 B2 | 7/2017 | Bray |
| 9,877,759 B2 | 1/2018 | Predick |
| 2001/0041894 A1 | 11/2001 | Campbell et al. |
| 2002/0004683 A1 | 1/2002 | Michelson |
| 2002/0045896 A1 | 4/2002 | Michelson |
| 2002/0045899 A1 | 4/2002 | Errico et al. |
| 2002/0111630 A1 | 8/2002 | Ralph et al. |
| 2002/0120273 A1 | 8/2002 | Needham et al. |
| 2002/0128655 A1 | 9/2002 | Michelson |
| 2002/0143336 A1 | 10/2002 | Hearn |
| 2002/0147450 A1 | 10/2002 | Lehuec et al. |
| 2002/0151899 A1 | 10/2002 | Bailey et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0023242 A1 | 1/2003 | Harrington |
| 2003/0040749 A1 | 2/2003 | Grabowski et al. |
| 2003/0060828 A1 | 3/2003 | Michelson |
| 2003/0083658 A1 | 5/2003 | Hawkes et al. |
| 2003/0105462 A1 | 6/2003 | Haider |
| 2003/0105526 A1 | 6/2003 | Bryant et al. |
| 2004/0034356 A1 | 2/2004 | Lehuec et al. |
| 2004/0068319 A1 | 4/2004 | Cordaro |
| 2004/0087951 A1 | 5/2004 | Khalili |
| 2004/0102773 A1 | 5/2004 | Morrison et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127899 A1 | 7/2004 | Konieczynski et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204712 A1 | 10/2004 | Kolb et al. |
| 2004/0220571 A1 | 11/2004 | Assaker et al. |
| 2004/0220572 A1 | 11/2004 | Michelson |
| 2004/0236335 A1 | 11/2004 | Michelson |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0043732 A1 | 2/2005 | Dalton |
| 2005/0059971 A1 | 3/2005 | Michelson |
| 2005/0075633 A1 | 4/2005 | Ross |
| 2006/0162506 A1 | 7/2006 | Kirchgaessler |
| 2006/0206208 A1 | 9/2006 | Michelson |
| 2007/0038303 A1 | 2/2007 | Myerson et al. |
| 2008/0149569 A1 | 6/2008 | Rai et al. |
| 2008/0249569 A1 | 10/2008 | Waugh et al. |
| 2009/0088808 A1 | 4/2009 | Lindemann et al. |
| 2009/0105830 A1 | 4/2009 | Jones et al. |
| 2009/0105831 A1 | 4/2009 | Jones et al. |
| 2009/0287249 A1 | 11/2009 | Reynolds et al. |
| 2010/0106249 A1 | 4/2010 | Tyber et al. |
| 2010/0145459 A1 | 6/2010 | McDonough et al. |
| 2010/0145460 A1 | 6/2010 | McDonough et al. |
| 2010/0152785 A1 | 6/2010 | Forton et al. |
| 2010/0249935 A1 | 9/2010 | Slivka et al. |
| 2010/0312345 A1 | 12/2010 | Duffield et al. |
| 2011/0009966 A1 | 1/2011 | Michelson |
| 2011/0166658 A1 | 7/2011 | Garber et al. |
| 2011/0178559 A1 | 7/2011 | Barry |
| 2011/0230969 A1 | 9/2011 | Biedermann et al. |
| 2012/0065734 A1 | 3/2012 | Barrett et al. |
| 2012/0126532 A1 | 5/2012 | Herndon |
| 2012/0191211 A1 | 7/2012 | Drozd |
| 2012/0203348 A1 | 8/2012 | Michelson |
| 2012/0215318 A1 | 8/2012 | Michelson |
| 2012/0232599 A1 | 9/2012 | Schoenly et al. |
| 2012/0265301 A1 | 10/2012 | Demers et al. |
| 2013/0218279 A1 | 8/2013 | Michelson |
| 2013/0245688 A1 | 9/2013 | Biedermann et al. |
| 2013/0268008 A1 | 10/2013 | McDonough et al. |
| 2014/0142705 A1 | 5/2014 | Duffield et al. |
| 2014/0163684 A1 | 6/2014 | Donner et al. |
| 2014/0188239 A1 | 7/2014 | Cummings |
| 2014/0277186 A1 | 9/2014 | Granberry et al. |
| 2015/0012050 A1 | 1/2015 | Anderson |

(56) References Cited

U.S. PATENT DOCUMENTS

| | | |
|---|---|---|
| 2015/0025637 A1 | 1/2015 | Moskowitz et al. |
| 2015/0032115 A1 | 1/2015 | Laposta et al. |
| 2015/0164564 A1 | 6/2015 | Reiley |
| 2015/0216675 A1 | 8/2015 | McDonough et al. |
| 2015/0238317 A1 | 8/2015 | Bonutti |
| 2015/0305883 A1 | 10/2015 | Garber et al. |
| 2016/0228257 A1 | 8/2016 | Predick et al. |

FOREIGN PATENT DOCUMENTS

| | | |
|---|---|---|
| EP | 0179695 A1 | 4/1986 |
| EP | 0313762 A1 | 5/1989 |
| FR | 2651996 A3 | 3/1991 |
| WO | WO 91/03994 A1 | 4/1991 |
| WO | WO 95/30389 A1 | 11/1995 |
| WO | WO 96/03096 A1 | 2/1996 |
| WO | WO 96/23457 A1 | 8/1996 |

OTHER PUBLICATIONS

Search Report and Written Opinion for International Application No. PCT/US2016/045722, dated Nov. 16, 2016, 12 pages.

IMPLANT FOR BONE FIXATION

CROSS-REFERENCE TO RELATED APPLICATIONS

This patent application is a division of U.S. application Ser. No. 14/819,761 filed Aug. 6, 2015, which is a is a continuation-in-part of U.S. application Ser. No. 14/616,239 filed Feb. 6, 2015, which claimed the benefit of and/or priority under 35 U.S.C. § 119(e) to U.S. provisional Application No. 61/936,644 filed Feb. 6, 2014. The entire contents of all of these applications are hereby specifically incorporated herein by reference

BACKGROUND

The present invention relates to implants for fixation of human bones, and particularly, to implants for fixation of bones of the foot. More particularly, the present invention relates to implants for internal fixation of calcaneus, tarsal, and metatarsal bones of the foot.

There are many reasons why surgeries are performed on the bones of the foot. Some foot surgeries such as osteotomies are performed to correct angular deformities. Other foot surgeries are performed to mend a fracture or to re-align or reposition bones of the foot. In these surgical procedures and others, two bone portions must be joined or otherwise connected to each other so as to be fixed in a desired position and, eventually fuse. This may be accomplished by a foot bone implant.

A foot bone implant in the shape of a wedge is typically inserted between the two bone portions or into the joint. The wedge, however, has to be retained in its insertion position by a plate placed over the joint. The plate can cause irritation to the adjacent anatomy as well as to the patient.

It is therefore evident from the above that there is a need for a foot bone implant in the shape of a wedge that overcomes the deficiencies of the prior art.

SUMMARY

The present invention is a wedge-shaped bone implant, system and method of use particularly, but not necessarily, for fixing bones of the foot. The wedge-shaped bone implant has bone screw bores that are each configured to hold a bone screw at a particular angle for receipt in a bone portion, thereby eliminating the need to also use a plate.

In one form, the wedge-shaped bone implant is moreover configured to receive a plate that aids in preventing a bone screw from backing out of its implant bore. The plate may be fastened to the wedge-shaped bone implant by one or more fastening screws. In this form, the top of the wedge-shaped implant has a recess that at least partially surrounds openings of the two implant bores. The recess is configured to receive the plate such that the plate at least partially obstructs the ability of a bone screw head within the implant bore to back out. Moreover, in this form, one or more of the threaded fastening screw bores for the fastening screws of the cover, may be used for engagement with an insertion instrument.

In another form, the wedge-shaped bone implant lacks a configuration on the top and thus does not accept a plate for covering the bone screws. In this case, a threaded bore may be provided for engagement with an insertion instrument instead of a threaded plate fastening screw bore.

One implant bore extends from the top of the implant body to one tapered side of the implant body, while the other implant bore extends from the top of the implant body to the other tapered side of the implant body. When installed, one bone screw projects from one tapered side of the shaped implant body, while the other bone screw extends from the other tapered side of the implant body. One bone screw thereby projects into one foot bone portion, while the other bone screw projects into the other bone screw portion, or different foot bones.

The bone implant can include an opening that extends through the implant body from one tapered side thereof to the other tapered side thereof. This opening allows the introduction and retention of bone graft material in order to promote bone fusion (i.e. a graft window). One tapered side of the body may also have teeth, serrations or the like that at least partially surround the graft window. The other tapered side may likewise also have teeth, serrations or the like that at least partially surround the graft window.

In one form, the implant body includes a through hole, bore, slot or the like in the distal aspect of the implant body. This allows for the insertion of a metallic component (e.g. titanium or tantalum) to allow for the visibility of the extent of the implant body in radiography, x-ray, or the like.

The present bone implant is thus characterized by an implant body in the general shape of a wedge, (e.g. as may be defined in solid geometry, as a right triangular prism with a rounded top, including a right oblique wedge in which the top edge is symmetrically shortened, causing the end triangles to slant obliquely) thus forming a right oblique wedge. The first bone screw bore extends from the rounded top to one slanted side of the wedge, while the second bone screw bore extends from the rounded top to the other slanted side of the wedge opposite the one side.

In one form, the outer configuration of the general wedge shape of the present foot bone implant may be modified from a traditional right oblique wedge shape to other wedge shapes or shapes incorporating a wedge structure. One such wedge modification provides a crescent or arced shaped wedge or a wedge in the shape of a crescent or arc. The crescent shaped wedge may include a threaded bore for engagement with an insertion instrument instead of a threaded plate fastening screw bore. The crescent shape also defines a bone graft opening or area that allows the introduction and retention of bone graft material in order to promote bone fusion. One tapered side of the implant body may also have teeth, serrations or the like that at least partially surround the graft opening. The other tapered side may likewise also have teeth, serrations or the like that at least partially surround the graft opening. The implant body may include a through hole, bore, slot or the like in the distal aspect of the implant body allowing for the insertion of a metallic component (e.g. titanium or tantalum) to allow for the visibility of the extent of the implant body in radiography, x-ray, or the like.

According to one method of use, the bone implant is placed into a bone joint to correct a deformity and provide fixation for fusion. The present bone implant permits the inclusion of bone screws to self-retain the wedge within the joint as well as providing stability for fusion. This is accomplished without the need for an additional plate.

According to another method of use, bone graft material is placed in the graft window, opening or area of the bone implant. The bone implant with bone graft material is then placed into a bone joint, bone osteotomy site, bone fracture or the like and provide fixation for fusion. The bone implant with bone graft material permits the inclusion of bone screws to self-retain the wedge within the joint as well as providing stability for fusion. Again, this is accomplished without the need for an additional plate.

Further aspects of the present invention will become apparent from consideration of the drawings and the following description of preferred forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of invention will be better understood by reference to the accompanying drawings which illustrate forms of the invention, wherein.

DETAILED DESCRIPTION

Figure 1:
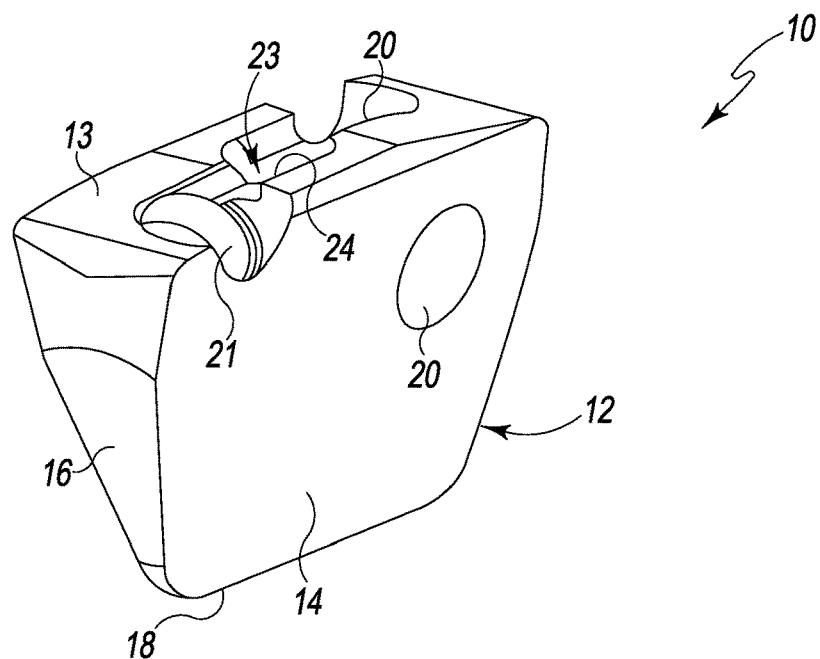
FIG. 1 is an isometric view of a wedge-shaped bone implant fashioned in accordance with the principles of the present invention.
Figure 2:
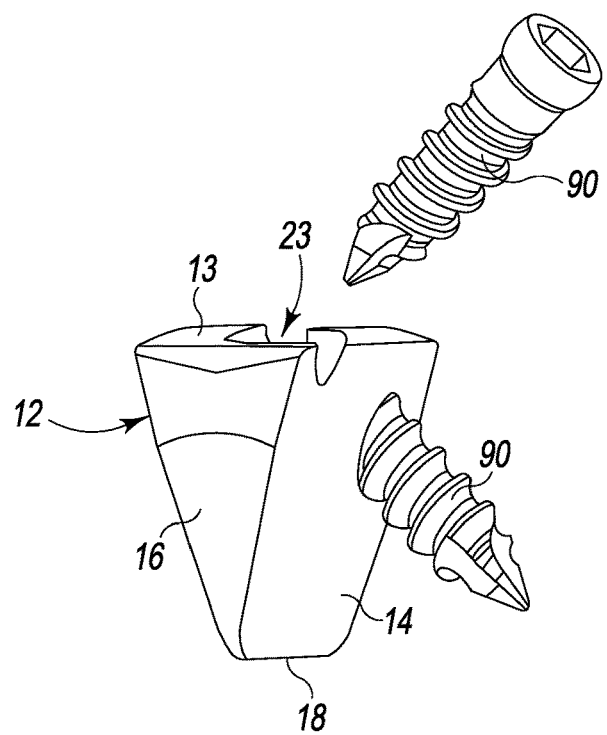
FIG. 2 is an isometric view of the wedge-shaped bone implant of FIG. 1 having a bone screw situated in the bone implant and another bone screw ready for insertion into the bone implant.

Referring to FIGS. 1-6 and, in particular FIG. 1, there is depicted a bone implant generally designated 10. The bone implant 10 is fashioned from a known biocompatible implant material and is used for aiding or providing internal fixation of calcaneus, tarsal, and metatarsal bones of the foot in cases such as, but not limited to, filling an osteotomy or expanding and correcting an angular deformity in the foot. The bone implant 10 may be used with other bones of the body such as the hand. However, the bone implant 10 will be described within this detailed description of the invention for us with bones of the foot and thus as a foot bone implant 10. The foot bone implant 10 has a generally wedge-shaped body 12 as wedges are defined in solid geometry and explained in the Summary of the Invention. As such, the body 12 has a generally rounded top 13, a generally planar first side 14, a generally planar second side 15 (see FIG. 4), a generally planar first end 16, a generally planar second end 17 (see FIG. 4), and a generally pointed bottom 18. The first and second sides 14 and 15 each slope inwardly from the top 13 to the bottom 18. The dimensions and angles of the foot bone implant 10 may be changed as desired in order to accommodate varying anatomies, purpose, and desired outcome. It should also be appreciated that the foot bone implant 10 and/or its principles are applicable to other bones of the body such as, but not limited to, the bones of the hand.

The body 12 has two bores 20, 21 each of which are dimensioned to receive a bone screw 90 such that the head of the bone screw is held by the body 12 and a portion of the tip and shank of the bone screw 90 extend from the body (see e.g., FIGS. 3-5) for receipt in a foot bone. The first bone screw bore 20 extends between the top 13 and the first side 14 such that the tip of a bone screw 90 extends from the first side 14 at an angle thereof. As particularly seen in FIG. 5, the opening of the first bone screw bore 20 on the top 13 of the body 12 is situated proximate to and on the edge between the top 13 and the second side 15 creating the angled bone screw bore 20. The second bone screw bore 21 extends between the top 13 and the second side 15 such that the tip of a bone screw 90 extends from the second side 15 at an angle thereof. As again particularly seen in FIG. 5, the opening of the second bone screw bore 21 on the top 13 of the body 12 is situated proximate to and on the edge between the top 13 and the first side 14 creating the angled second bone screw bore 21. Both bone screw bore openings on the top 13 of the body 12 are sized and configured to capture and retain the head of a bone screw. Moreover, both bone screw bore openings on the top 13 are configured such that the heads of the bone screws are countersunk relative to the surface of the top 13.

Figure 3:
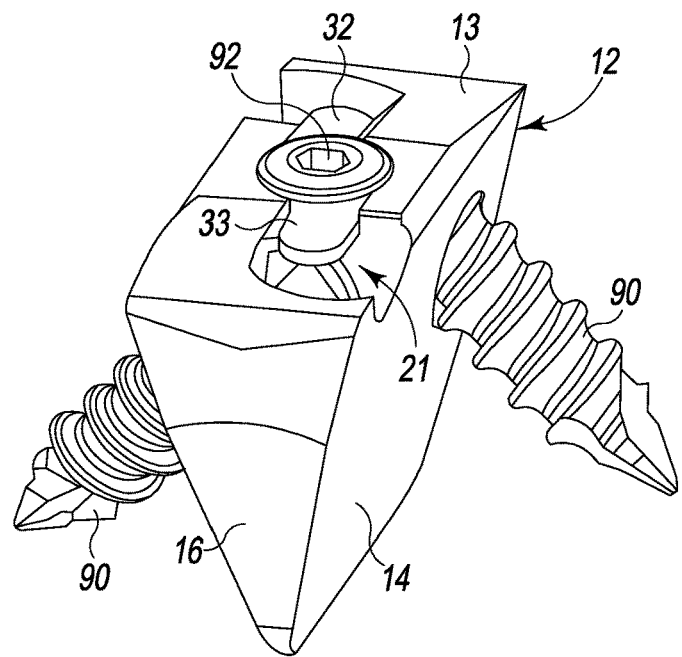
FIG. 3 is an isometric view of the wedge-shaped bone implant of FIG. 1 having two bone screws situated therein along with a screw retention plate, forming a bone implant system.
Figure 4:
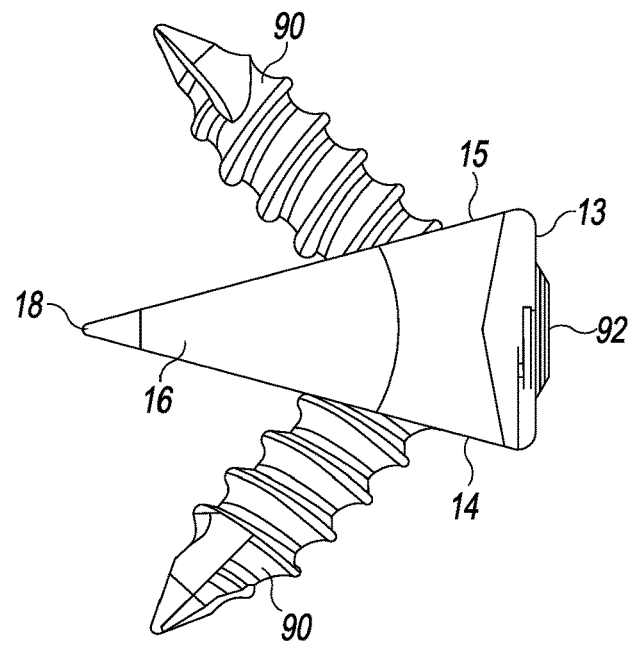
FIG. 4 is an end view of the bone implant system of FIG. 3.
Figure 5:
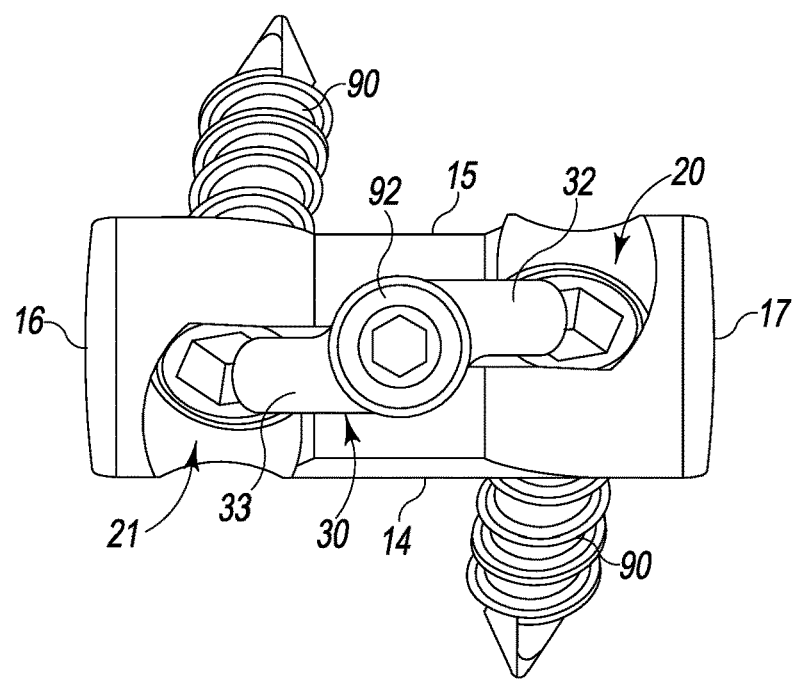
FIG. 5 is a top view of the bone implant system of FIG. 3.
Figure 6:
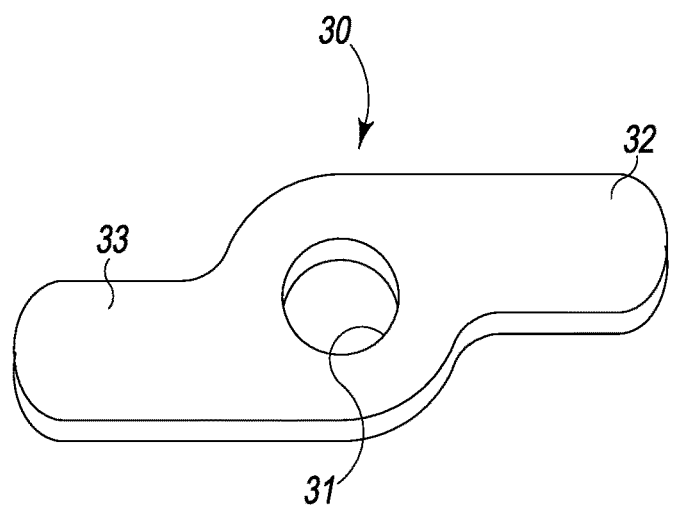
FIG. 6 is an isometric view of the bone screw retention cover/plate of the bone implant system of FIG. 3.

A configured recess, channel, groove, depression, or the like 23 is provided in the surface of the top 13. The recess 23 is in communication with the bone screw bore openings on the top 13. Additionally, a threaded bore 24 is provided in the body 12 within the recess 23 of the top 13, the threaded bore 24 configured to receive a threaded screw or fastener 92. The recess 23 is further configured to receive a cover or plate 30. As seen in FIG. 6, the cover 30, made from a biocompatible material, has hole 31 and first and second wings 32, 33. The cover 30 is shaped such that it fits into the recess 23. Preferably, but not necessarily, the cover 30 is shaped in similar manner to the recess 23. The cover 30 is received in the recess 23 such that the hole 31 is aligned with the threaded bore 24 in the top 13 of the body 12, with the first wing 32 extending over at least a part of the opening of first bone screw bore 20 and the second wing 33 extending over at least a part of the opening of the second bone screw bore 21. FIGS. 3 and 5 show the cover 30 mounted to the body 12 by the threaded screw 92. Two bone screws 90 are also situated in the body 12. The first wing 32 extends over or covers a portion of the bone screw head of the bone screw 90 that is in the first bone screw bore 20. The second wing 33 extends over or covers a portion of the bone screw head of the bone screw 90 that is in the second bone screw bore 21. The first and/or second wing may be shaped to extend over more of the bone screw head than shown. Because the wings are over the bone screw heads, this prevents the bone screw from backing out of the bone screw bore.

Referring to FIGS. 7-10, there is depicted a foot bone implant, generally designated 10a, being a variation of the foot bone implant 10. As such, the foot bone implant 10a is thus fashioned in a generally like manner to the foot bone implant 10, with the like features and/or components denoted by the addition of the letter "a" to the feature and/or component of the foot bone implant 10. Because these features and/or components are the same, they will not be discussed in detail. Reference should therefore be made to the foot bone implant 10 for details.

Figure 7:
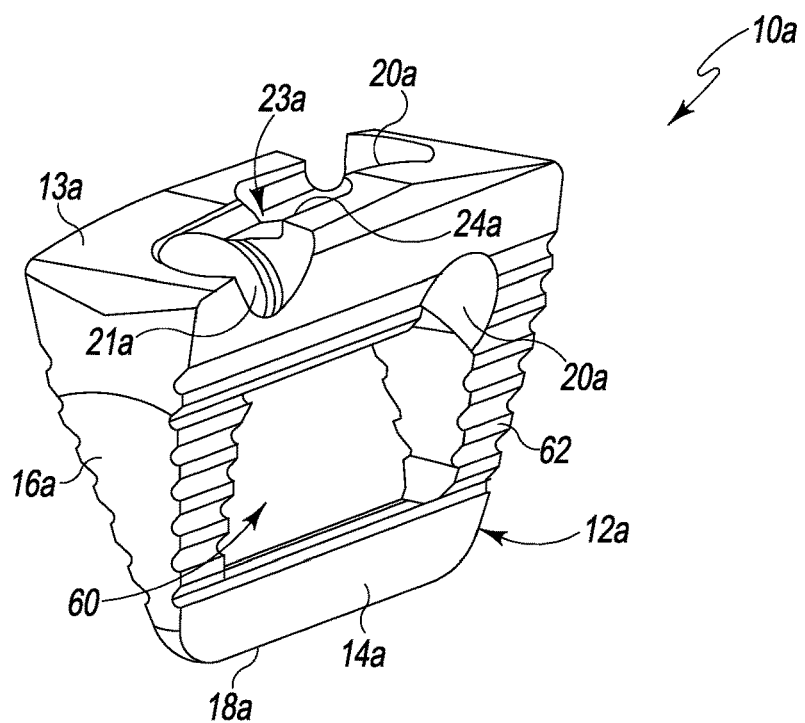
FIG. 7 is an isometric view of another wedge-shaped bone implant fashioned in accordance with the principles of the present invention.
Figure 8:
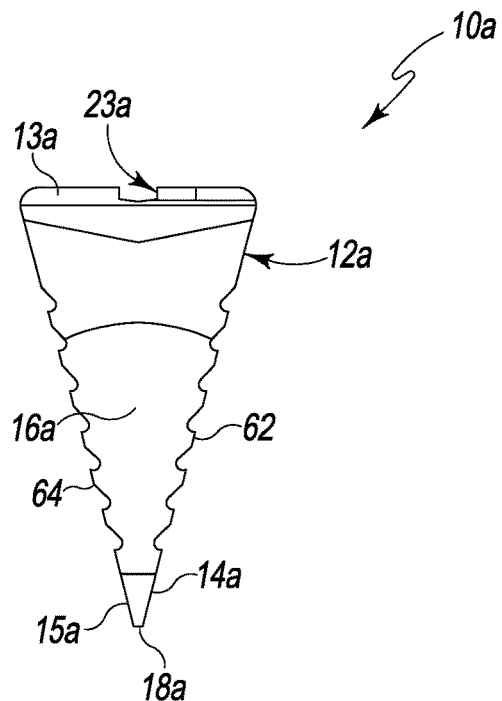
FIG. 8 is a side view of the bone implant of FIG. 7.
Figure 9:
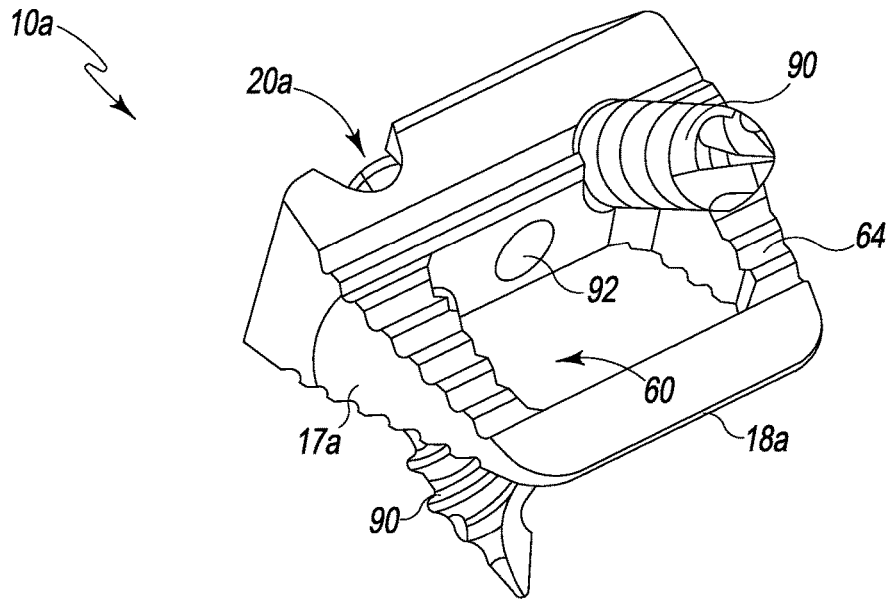
FIG. 9 is an isometric view of the bone implant of FIG. 8 having two bone screws situated therein.

As best seen in FIGS. 7 and 9, the foot bone implant body 12a has an opening 60 that extends from the one tapered or slanted side 14a to the other tapered or slanted side 15a. While the opening 60 is shown as rectangular, it should be appreciated that the opening 60 may be configured as desired. The opening 60 is used to receive and hold bone graft material. As such, the opening 60 may be considered a bone graft window or simply a graft window. The bone graft material may be of any kind. Moreover, the graft window may comprise two or more openings that each extend from the one tapered or slanted side 14a to the other tapered or slanted side 15a. These graft openings can be shaped as desired.

Figure 10:
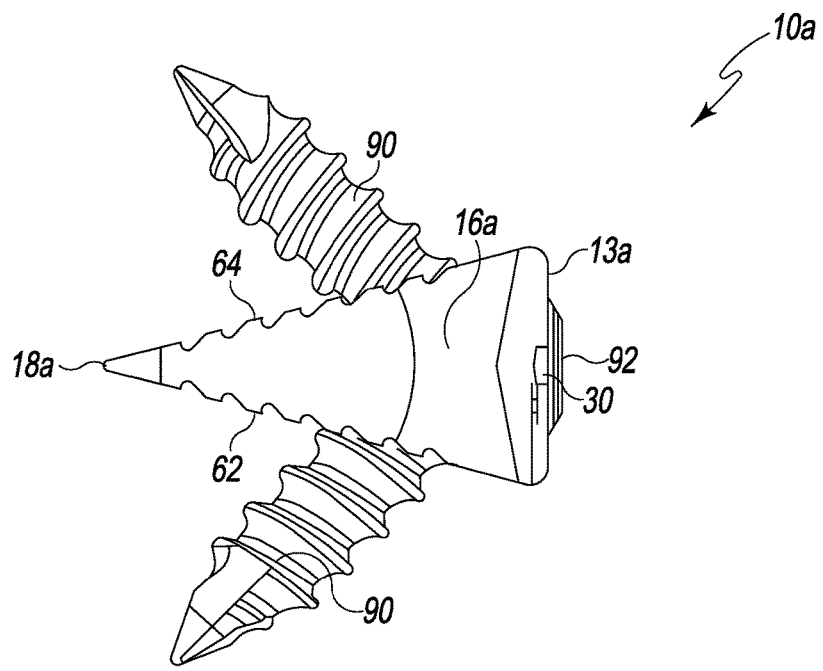
FIG. 10 is a side view of the bone implant with bone screws of FIG. 9.

As seen in FIGS. 9 and 10, the two bone screws 90 are shown situated in the body 12a such as they would appear when implanted. The bone screw cover 30 is within the top recess 23a and fastened to the body 12a via the fastener 92. As per the foot bone implant 10, portions of the cover 30 extend over the bone screw heads in order to prevent the bone screws from backing out.

In addition to the bone graft window 60, the body 12a has features for aiding in and/or promoting fusion between two foot bones or foot bone portions. These features also aid in keeping the body 12a in place. Particularly, a portion of the one tapered or slanted side 14a has teeth, serrations or the like 62, while a portion of the other tapered or slanted side 15a likewise has teeth, serrations or the like 64. The teeth 62 surround the graft window 60 or at least are present about the top and sides of the graft window 60 in the slanted side 14a. Likewise, the teeth 64 surround the graft window 60 or at least are present about the top and sides of the graft window 60 in the slanted side 15a. The upper portions of the slanted sides 14a and 15a proximate the top 13a and the lower portions of the slanted sides 14a, 15a proximate the bottom 18a preferably, but not necessarily, lack teeth, serrations, or the like.

Referring to FIGS. 11-15, there is depicted a foot bone implant, generally designated 10b, being a variation of the foot bone implants 10 and/or 10a. As such, the foot bone implant 10b is thus fashioned in a generally like manner to the foot bone implants 10, 10a, with the like features and/or components denoted by the addition of the letter "b" to the feature and/or component of the foot bone implants 10, 10a. Because these features and/or components are the same, they will not be discussed in detail. Reference should therefore be made to the foot bone implants 10, 10a for details.

Figure 11:
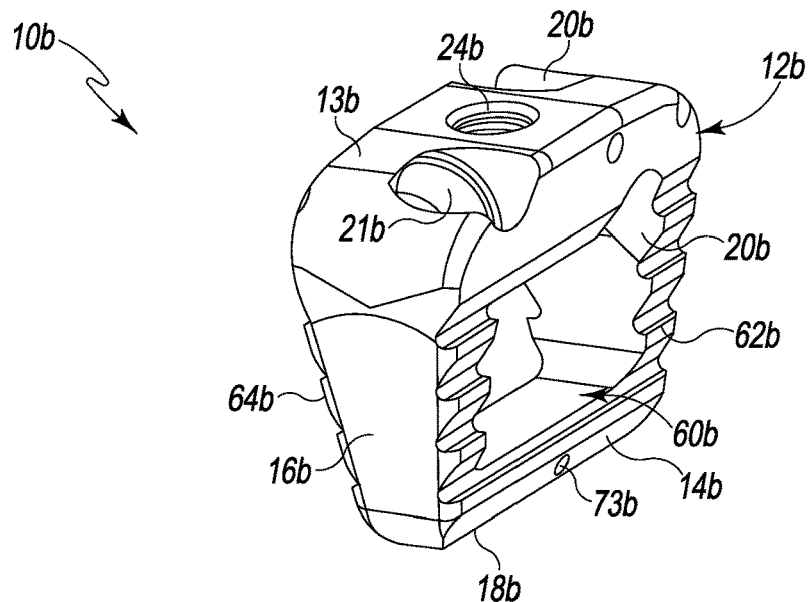
FIG. 11 is an isometric view of another wedge-shaped bone implant fashioned in accordance with the principles of the present invention.
Figure 12:
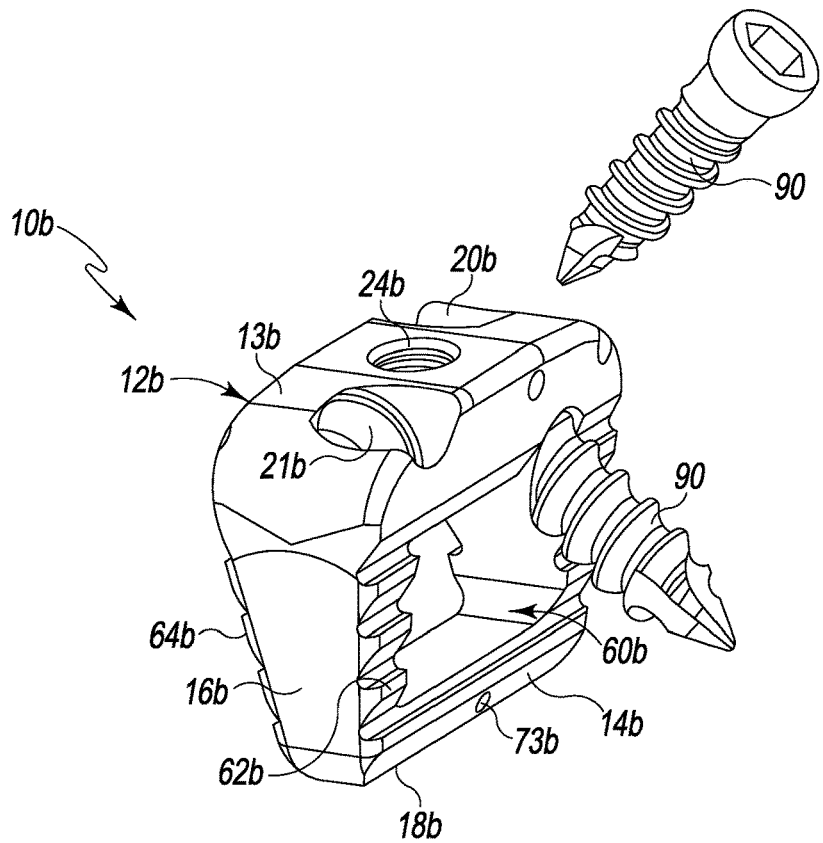
FIG. 12 is an isometric view of the wedge-shaped bone implant of FIG. 11 having a bone screw situated in the bone implant and another bone screw ready for insertion into the bone implant.
Figure 13:
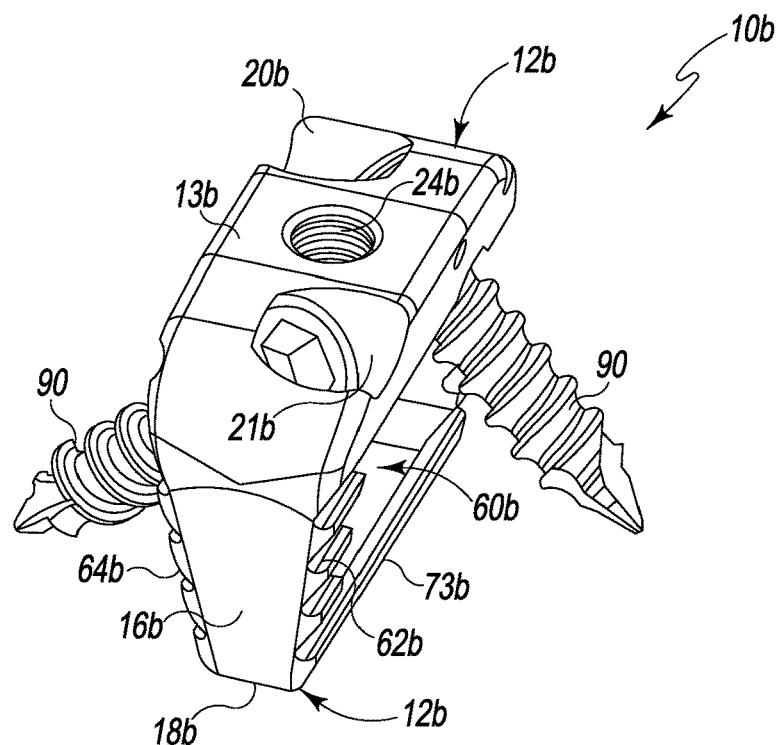
FIG. 13 is an isometric view of the wedge-shaped bone implant of FIG. 11 having two bone screws situated therein, forming another foot bone implant system.

As best seen in FIGS. 11-13, the foot bone implant body 12b has an opening 60b that extends from the one tapered or slanted side 14b to the other tapered or slanted side 15b. While the opening 60b is shown as rectangular, it should be appreciated that the opening 60b may be configured as desired. The opening 60b is used to receive and hold bone graft material. As such, the opening 60b may be considered a bone graft window or simply a graft window. The bone graft material may be of any kind. Moreover, the graft window may comprise two or more openings that each extend from the one tapered or slanted side 14b to the other tapered or slanted side 15b. These graft openings can be shaped as desired.

Figure 14:
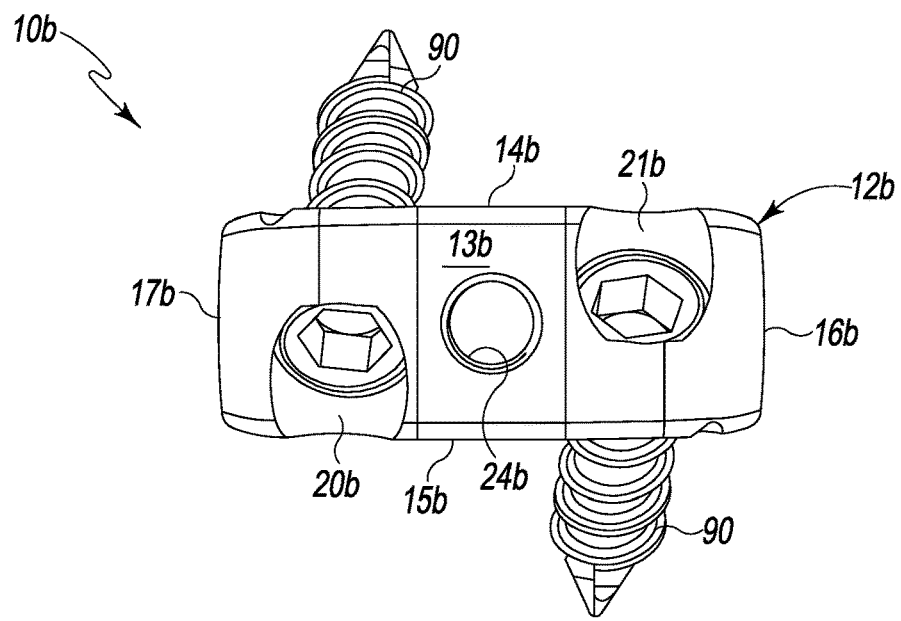
FIG. 14 is a top view of the bone implant system of FIG. 13.
Figure 15:
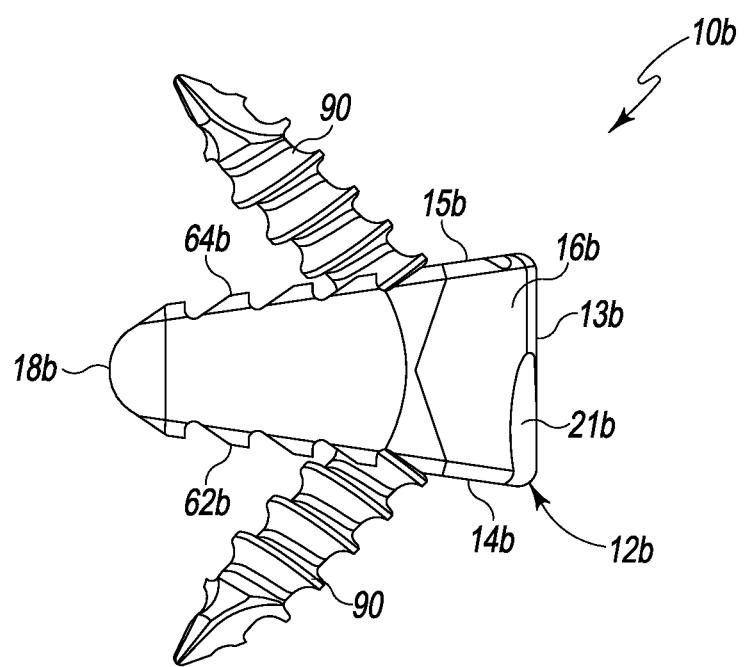
FIG. 15 is an end view of the bone implant system of FIG. 13.

As seen in FIGS. 13-15, the two bone screws 90 are shown situated in the body 12b such as they would appear when implanted. In addition to the bone graft window 60b, the body 12b has features for aiding in and/or promoting fusion between two foot bones or foot bone portions. These features also aid in keeping the body 12b in place. Particularly, at least a portion or more of the one tapered or slanted side 14b has teeth, serrations or the like 62b, while at least a portion or more of the other tapered or slanted side 15b likewise has teeth, serrations or the like 64b. The teeth 62b surround the graft window 60b or at least are present about the top and sides of the graft window 60b in the slanted side 14b. Likewise, the teeth 64b surround the graft window 60b or at least are present about the top and sides of the graft window 60b in the slanted side 15b. The upper portions of the slanted sides 14b and 15b proximate the top 13b and the lower portions of the slanted sides 14b, 15b proximate the bottom 18b preferably, but not necessarily, lack teeth, serrations, or the like. It should be appreciated that any pattern of teeth, direction of teeth, and/or dimensions of teeth may be used.

As best seen in FIGS. 11-14, the top 13b of the implant body 12b lacks a configuration on the top for a cover and thus does not accept a plate for covering the bone screws like foot implants 10 and 10a. In this case, a threaded bore 24b may be provided for engagement with an insertion instrument (not shown) instead of a threaded plate fastening screw bore.

As best seen in FIGS. 11-12, the implant body 12b includes a through hole, bore, slot or the like 73b in the distal aspect 18b of the implant body 12b. This allows for the insertion of a metallic component such as titanium or tantalum (not shown) to allow for the visibility of the extent of the implant body in radiography, x-ray, or the like.

Referring to FIGS. 16-21, there is depicted another foot bone implant, generally designated 10c, being a variation or modification from the traditional right oblique wedge shape foot bone implants 10, 10a, and 10b. However, the foot bone implant 10c is fashioned in a generally like manner to the foot bone implants 10, 10a, and 10b, and thus like features and/or components are denoted by the addition of the letter "c" to the feature and/or component of the foot bone implants 10, 10a, 10b. Because these features and/or components are at least generally the same, some will not necessarily be discussed in detail. Reference should therefore be made to the foot bone implants 10, 10a, and 10b for details if necessary. The foot bone implant 10c is fashioned from a known biocompatible implant material and is used for aiding or providing internal fixation of calcaneus, tarsal, and metatarsal bones of the foot in cases such as, but not limited to, filling an osteotomy or expanding and correcting an angular deformity in the foot. Other uses are contemplated.

The foot bone implant 10c has a body 12c generally in the form of a crescent or arced shaped wedge or a wedge in the shape of a crescent or arc. The crescent shaped wedge body 12c has a generally curved top 13c, a generally planar first side 14c, a generally planar second side 15c, a generally curved first end 16c, a generally curved second end 17c, and a curved bottom 18c forming first and second legs 19a, 19b. The first and second sides 14c and 15c each slope, slant or incline inwardly from the curved top 13c to the curved bottom 18c. The body 12c further includes a threaded bore 24c for engagement with an insertion instrument (not shown) instead of a threaded plate fastening screw bore. The dimensions and angles of the foot bone implant 10c may be changed as desired in order to accommodate varying anatomies, purpose, and desired outcome. It should also be appreciated that the foot bone implant 10c and/or its principles are applicable to other bones of the body such as, but not limited to, bones of the hand.

The body 12c has two bores 20c, 21c each of which are dimensioned to receive a bone screw 90 such that the head of the bone screw is held by the body 12c and a portion of the tip and shank of the bone screw 90 extend from the body for receipt in a bone. The first bone screw bore 20c extends between the curved top 13c and the first side 14c such that the tip of a bone screw 90 extends from the first side 14c at an angle thereof. As particularly seen in FIG. 19, the opening of the first bone screw bore 20c on the curved top 13c of the body 12c is situated proximate to and between the curved top 13c and the second side 15c creating the angled bone screw bore 20c. The second bone screw bore 21c extends between the curved top 13c and the second side 15c such that the tip of a bone screw 90 extends from the second side 15c at an angle thereof. As again particularly seen in FIG. 19, the opening of the second bone screw bore 21c on the curved top 13c of the body 12c is situated proximate to and between the curved top 13c and the first side 14c creating the angled second bone screw bore 21c. Both bone screw bore openings on the curved top 13c of the body 12c are sized and configured to capture and retain the head of the bone screw 90. Moreover, both bone screw bore openings 20c, 21c on the curved top 13c are configured such that the heads of the bone screws 90 are countersunk relative to the surface of the curved top 13c.

Figure 16:
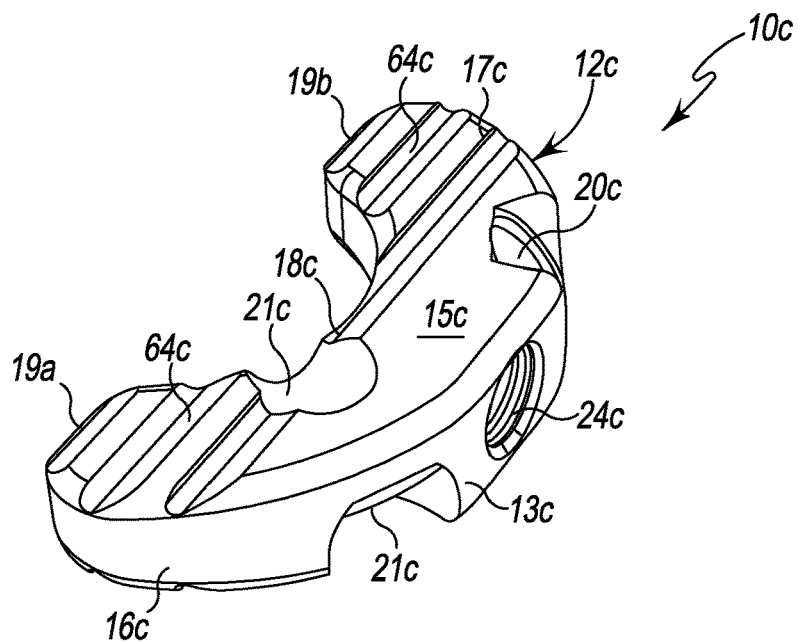
FIG. 16 is an isometric view of another wedge-shaped bone implant fashioned in accordance with the principles of the present invention.
Figure 17:
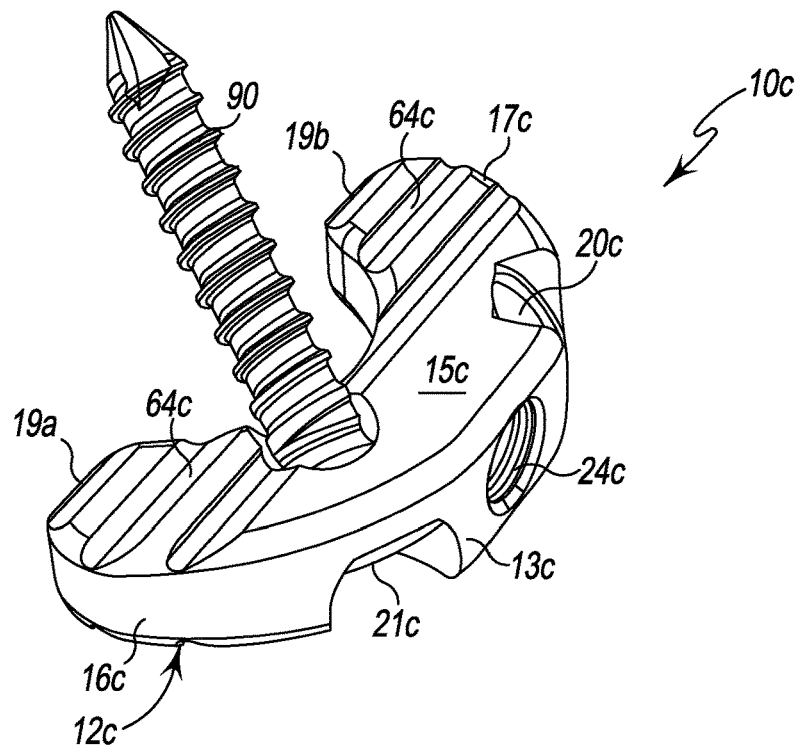
FIG. 17 is an isometric view of the wedge-shaped bone implant of FIG. 16 having a bone screw situated in the bone implant.
Figure 18:
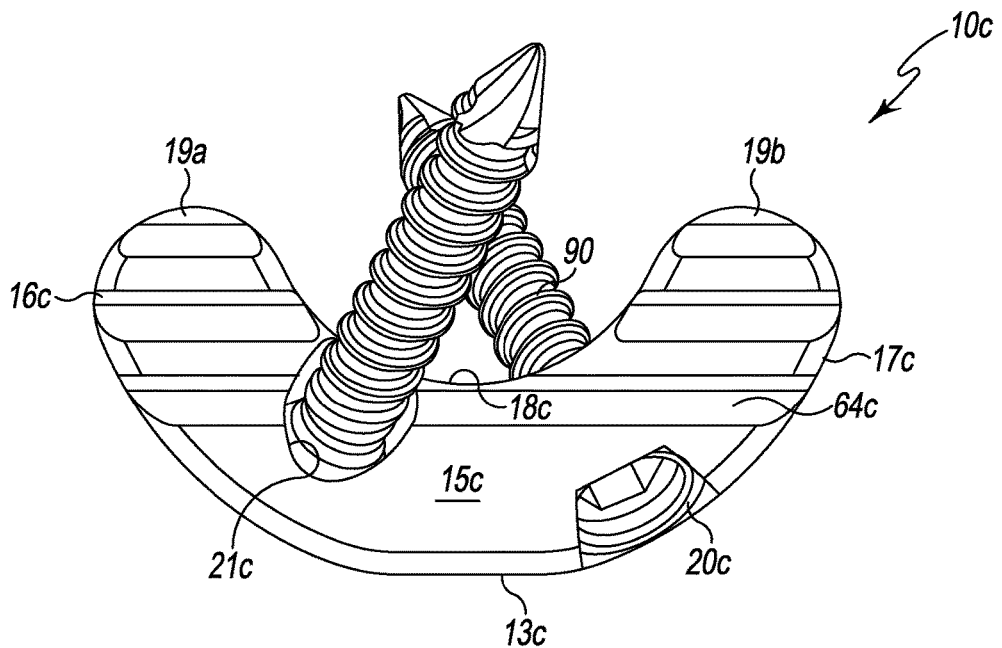
FIG. 18 is a top view of the wedge-shaped bone implant of FIG. 16 having two bone screws situated in the bone implant.
Figure 19:
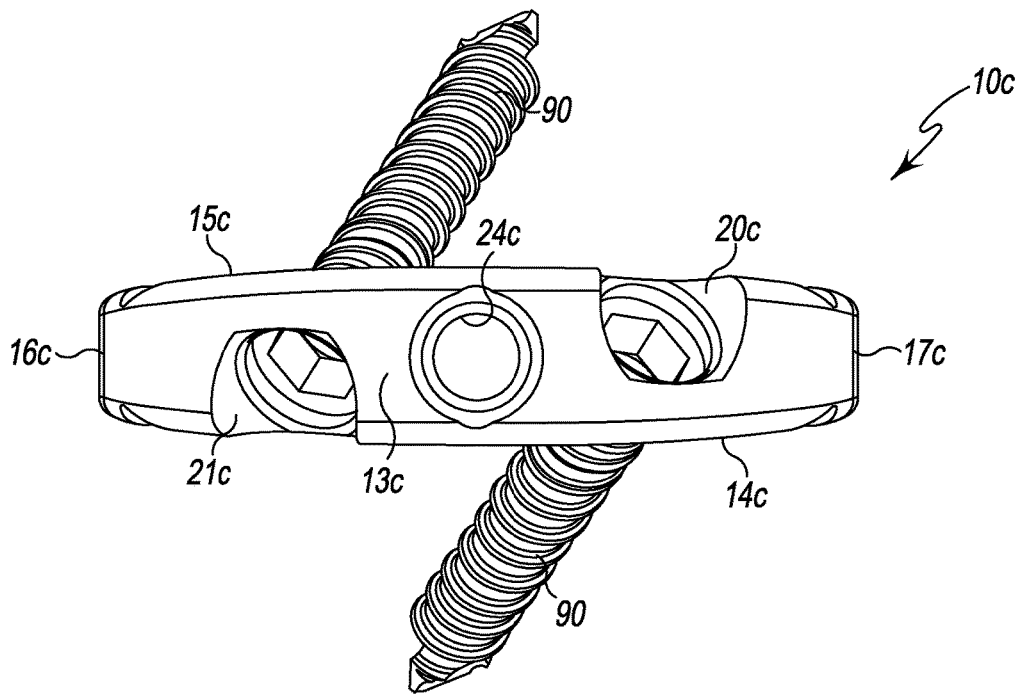
FIG. 19 is an top end view of the wedge-shaped bone implant of FIG. 16 having two bone screws situated in the bone implant.
Figure 20:
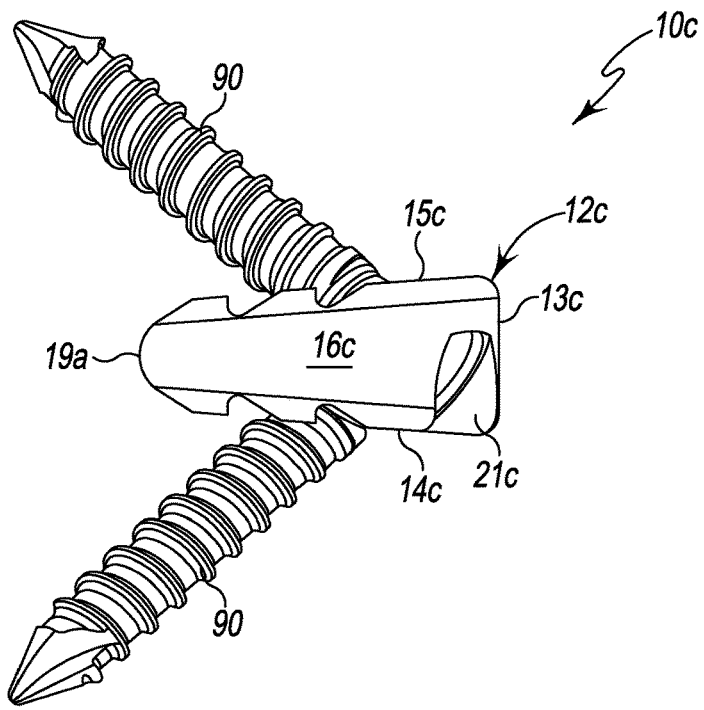
FIG. 20 is a side view of the wedge-shaped bone implant of FIG. 16 having two bone screws situated in the bone implant.
Figure 21:
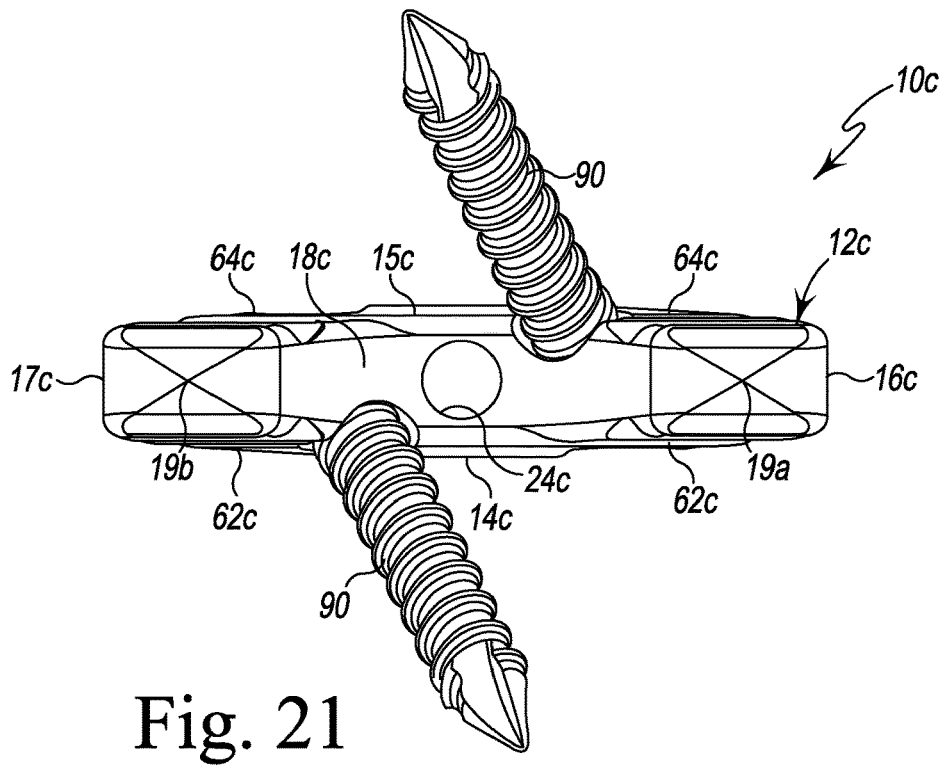
FIG. 21 is a bottom end view of the wedge-shaped bone implant of FIG. 16 having two bone screws situated in the bone implant.

As best seen in FIGS. 16-18, because the bone implant body 12c is crescent shaped, the bottom 18c between the first and second legs 19a, 19b defines an opening that may be used to receive and hold bone graft material. As such, the crescent shaped opening defined by the curved bottom 18c may be considered a bone graft opening or area. Since the curved bottom 18c faces into the bone when implanted (see FIG. 22), the bone graft material is held within the bone draft opening. The bone graft material may be of any kind.

As seen in FIGS. 18-21, the two bone screws 90 are shown situated in the body 12c such as they would appear when implanted. In addition to the bone graft opening defined between the first and second legs 19a, 19b of the curved bottom 18c, the body 12c has features for aiding in and/or promoting fusion between two bones or bone portions. These features also aid in keeping the body 12c in place. Particularly, at least a portion or more of the slanted side 14c has teeth, serrations or the like 62c, while at least a portion or more of the other slanted side 15c likewise has teeth, serrations or the like 64c. The teeth 62c surround the graft opening. Likewise, the teeth 64c surround the graft opening. The upper portions of the slanted sides 14c and 15c proximate the curved top 13c preferably, but not necessarily, lack teeth, serrations, or the like. It should be appreciated that any pattern of teeth, direction of teeth, and/or dimensions of teeth may be used.

While not shown in the figures, the implant body 12c may include a through hole, bore, slot or the like in the distal aspect of the implant body 12c. This allows for the insertion of a metallic component such as titanium or tantalum (not shown) to allow for the visibility of the extent of the implant body in radiography, x-ray, or the like.

Figure 22:
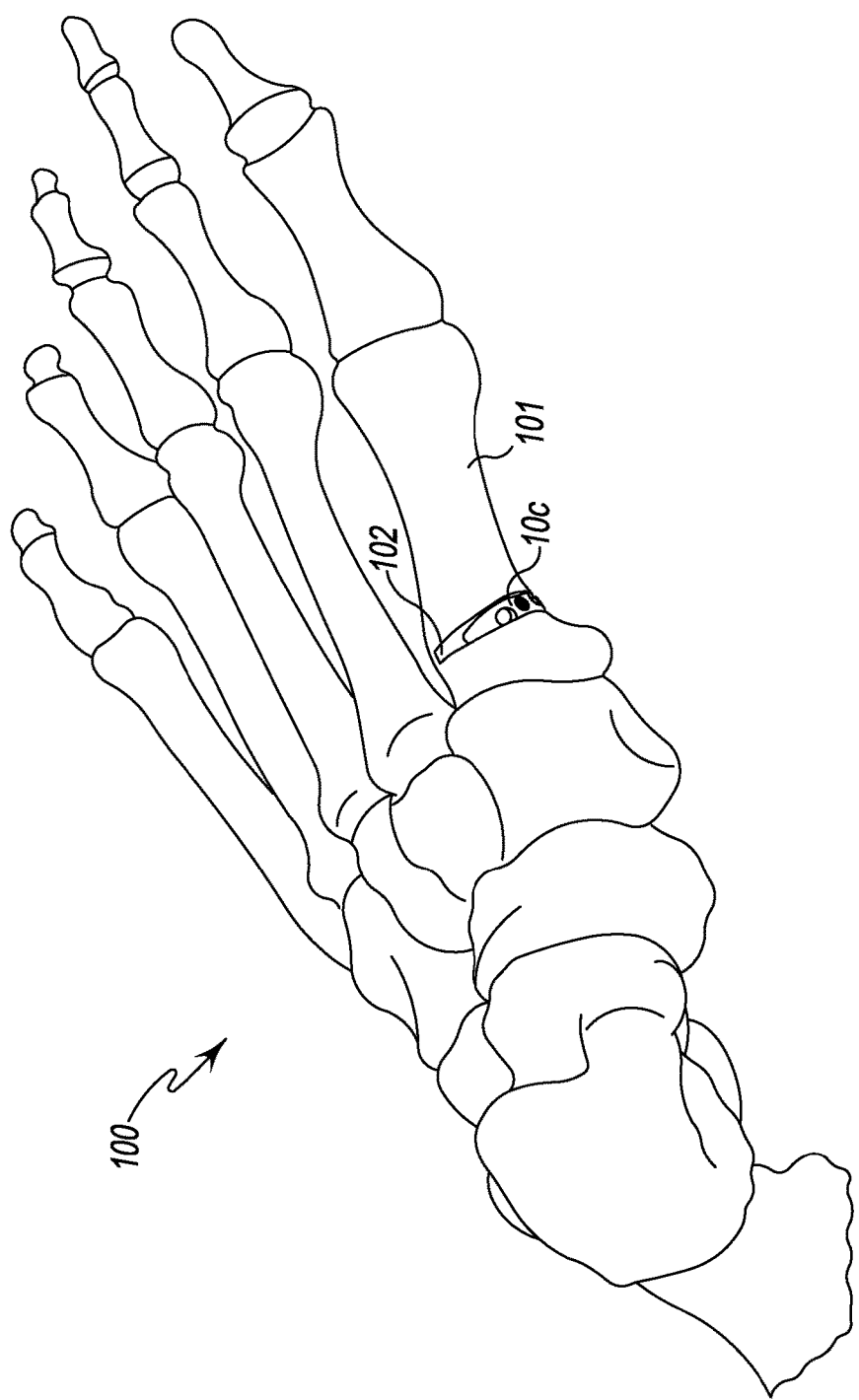
FIG. 22 is a view of bones of a left foot with the wedge-shaped bone implant of FIG. 16 implanted in a fracture or osteotomy cut of the first metatarsal of the foot.

Referring to FIG. 22 bones of a left human foot, generally designated 100, are depicted. The first metatarsal 101 of the foot 100 has had a fracture or osteotomy cut 102 into which the bone implant 10c (with or without bone graft material) has been implanted.

It should be appreciated that although the present bone fixation device has been shown in the figures and described above in particularity with respect to bones of the foot, such is applicable to bones of the hand; those bones being very similar in anatomy. It should also be appreciated that dimensions of the body and its features and/or components can be changed as desired.

What is claimed is:
1. A method of joining a first bone portion and a second bone portion, the method comprising the steps of:
  (a) providing a bone implant comprising:
    a crescent shaped body defining:
      a curved top having a first width;
      an arced bottom defining a first leg at a first end of the arced bottom and a second leg at a second end of the arced bottom, the first and second legs having a second width that is less than the first width of the curved top, wherein the first leg and the second leg define a graft space therebetween configured to receive bone graft material;
      a first slanted side extending from a first curved side of the curved top to the first and second legs of the arced bottom, wherein the first slanted side includes a serrated portion surrounding the graft space and a non-serrated space proximate the curved top;
      a second slanted side opposite the first slanted side, wherein the second slanted side extends from a second curved side of the curved top to the first and second legs of the arced bottom;
      a first curved lateral side, wherein the first curved lateral side extends from a first curved lateral side of the curved top to the first leg of the arced bottom; and
      a second curved lateral side opposite the first curved lateral side, wherein the second curved lateral side extends from a second curved lateral side of the curved top to the second leg of the arced bottom;
    a first bore extending from the first curved lateral side of the curved top to the second slanted side; and a second bore extending from the second curved lateral side of the curved top to the first slanted side;
(b) providing a first bone screw and a second bone screw;
(c) implanting the bone implant between the first bone portion and the second bone portion; and
(d) securing the bone implant to the first and second bone portions via the first and second bone screws.

2. The method of claim 1, further comprising the step of providing bone graft material with the bone implant during implantation.

3. The method of claim 1, further comprising implanting bone graft material between the first leg and the second leg of the arced bottom of the crescent shaped body.

4. The method of claim 1, wherein the curved top includes a threaded bore between the first bore and the second bore.

5. The method of claim 4, further comprising the step of providing an insertion instrument and engaging the threaded bore with the insertion instrument.

6. The method of claim 1, wherein the crescent shaped body further comprises first serrations on the first slanted side for engaging the first bone portion.

7. The method of claim 6, wherein the crescent shaped body further comprises second serrations on the second slanted side for engaging the second bone portion.

8. The method of claim 7, wherein:
the first serrations of the first slanted side extend from the first and second legs of the curved bottom to first and second bores in the first slanted side; and
the second serrations of the second slanted side extend from the first and second legs of the curved bottom to first and second bores in the second slanted side.

9. A method of joining a first bone portion and a second bone portion, the method comprising the steps of:
(a) providing a crescent shaped wedge defining:
a curved top of a first width;
a crescent shaped bottom defining a first leg at a first end of the crescent shaped bottom and a second leg at a second end of the crescent shaped bottom, the first and second legs having a second width that is less than the first width of the curved top;
a first side extending from a first curved side of the curved top to the first and second legs of the crescent shaped bottom, wherein the first side includes a serrated portion proximate the crescent shaped bottom and a non-serrated space proximate the curved top;
a second side opposite the first side extending from a second curved side of the curved top to the first and second legs of the crescent shaped bottom;
a first curved lateral side extending from a first curved lateral side of the curved top to the first leg of the crescent shaped bottom; and
a second curved lateral side opposite the first curved lateral side, the second curved lateral side extending from a second curved lateral side of the curved top to the second leg of the crescent shaped bottom;
a first bore extending from the first curved lateral side of the curved top to the second side; and
a second bore extending from the second curved lateral side of the curved top to the first side;
(b) providing a first bone screw and a second bone screw;
(c) implanting the bone implant between the first bone portion and the second bone portion; and
(d) securing the bone implant to the first bone portion by the first bone screw, and to the second bone portion by the second bone screw.

10. The method of claim 9, further comprising the step of providing bone graft material with the bone implant during implantation.

11. The method of claim 9, further comprising implanting bone graft material between the first leg and the second leg of the crescent shaped bottom of the crescent shaped wedge.

12. The method of claim 9, wherein the curved top includes a threaded bore between the first bore and the second bore.

13. The method of claim 12, further comprising the step of providing an insertion instrument and engaging the threaded bore with the insertion instrument.

14. The method of claim 9, wherein the crescent shaped wedge further comprises first serrations on the first side for engaging the first bone portion.

15. The method of claim 14, wherein the crescent shaped wedge further comprises second serrations on the second side for engaging the second bone portion.

16. The method of claim 15, wherein:
the first serrations of the first side extend from the first and second legs of the crescent shaped bottom to first and second bores in the first side; and
the second serrations of the second side extend from the first and second legs of the crescent shaped bottom to first and second bores in the second side.

* * * * *